United States Patent [19]

Ranade

[11] Patent Number: 5,633,240
[45] Date of Patent: May 27, 1997

[54] PARENTERAL SOLUTIONS CONTAINING METOLAZONE

[75] Inventor: Vasant Ranade, Libertyville, Ill.

[73] Assignee: Academic Pharmaceuticals, Lake Bluff, Ill.

[21] Appl. No.: 387,477

[22] Filed: Feb. 13, 1995

Related U.S. Application Data

[63] Continuation-in-part of Ser. No. 299,493, Sep. 1, 1994.

[51] Int. Cl.$^6$ .......................... A61K 31/63; A61K 31/505
[52] U.S. Cl. .......................... 514/155; 514/258; 514/259
[58] Field of Search .................... 514/258, 259, 514/155

[56] References Cited

U.S. PATENT DOCUMENTS

| | | | |
|---|---|---|---|
| 2,174,242 | 9/1939 | Hass et al. | 564/507 |
| 2,485,982 | 10/1949 | McMillan | 204/77 |
| 3,058,882 | 10/1962 | Stürm et al. | 514/155 |
| 3,360,518 | 12/1967 | Shetty | 544/288 |
| 3,557,111 | 1/1971 | Shetty | 544/288 |
| 5,124,152 | 6/1992 | Biringer et al. | 424/422 |

OTHER PUBLICATIONS

Windholz et al., *The Merck Index*, 10th Ed. (Merck & Co., Inc) (New Jersey) 1983, p. 615, ab. No. 4186 and p. 1395, ab. No. 9575.

*Primary Examiner*—Kevin E. Weddington
*Attorney, Agent, or Firm*—John J. McDonnell; Steven J. Sarussi

[57] ABSTRACT

Disclosed herein are parenteral solutions containing 7-halo-1,2,3,4-tetrahydro-3-aryl-6-quinazoline sulfonamide in Tris or Bis-Tris or Tris buffer useful in the treatment of hypertension, heart disease and heart failure and renal disease. Also disclosed are methods for preparing such solutions.

7 Claims, No Drawings

PARENTERAL SOLUTIONS CONTAINING METOLAZONE

BACKGROUND OF THE INVENTION

1. Field of the Invention

This application is a continuation-in-part of pending U.S. application Ser. No. 08/299,493 filed Sep. 1, 1994.

The present invention relates to parenteral solutions containing 7-Halo-1,2,3,4-tetrahydro-3-aryl-6-qinazoline sulfonamide.

2. Description of the Related Art

Metolazone is a quinazoline diuretic approved for use in an oral tablet form (MYKROX®) for the treatment of hypertension, alone or in combination with other antihypertensive drugs of a different class. This compound acts primarily to inhibit sodium reabsorption at the cortical diluting site and to a lesser extent in the proximal convoluted tubule. Sodium and chloride ions are excluded in approximately equivalent amounts. The increased delivery of sodium to the distal-tubular exchange site results in increased potassium excretion.

To treat hypertension, the compound may be administered in oral dosage forms such as in the form of a tablet containing from 0.5–10 mg of metolazone, or it may be administered in the form of an intravenous solution.

Metolazone is also indicated for use in treating heart failure and renal disease. Further, when metolazone is combined with furosemide (lasix), the effectiveness of the diuretics is greatly enhanced. Furosemide can be administered intravenously to obtain the best and most rapid effect in emergencies. However, there is no intravenous formulation available of metolazone since metolazone is sparingly soluble in most solvents. Metolazone is only sparingly soluble in water, but is said to be somewhat more soluble in plasma, blood, alkali and organic solvents.

U.S. Pat. Nos. 3,360,518 and 3,557,111 disclose methods for preparing metolazone.

DESCRIPTION OF THE INVENTION

The present invention provides parenteral solutions comprising as an active ingredient a 7-Halo-1,2,3,4-tetrahydro-3-aryl-6-quinazoline sulfonamide of the following formula:

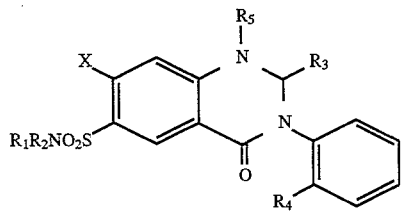

wherein X is a halogen;

$R_1$, $R_2$, $R_3$ and $R_4$ are independently selected from hydrogen and alkyl groups having from about 1 to 6 carbon atoms; and $R_5$ is hydrogen or an alkyl group having from about 1 to 6 carbon atoms.

More specifically, the present invention provides parenteral solutions suitable for intravenous administration containing as an active ingredient an effective anti-hypertensive amount of 7-chloro-1,2,3,4-tetrahydro-2-methyl-3-(-2-methylphenyl)-4-oxo-6-quinazoline sulfonamide (metolazone) in a sterile solvent comprising a [bis-(2-hydroxyethyl)-amino]tris-(hydroxymethyl)methane (Bis-Tris) buffer having a pH from about 10.5 to 12.5, and preferably from 11.5 to 12, i.e., metolazone-Bis-Tris solutions.

The invention further provides parenteral solutions suitable for intravenous administration containing Metolazone as an active ingredient in a sterile solvent comprising a Tris-(hydroxymethyl) amino methane, hydrochloride (Tris) buffer having a pH of from about 10.5 to 12.5, and preferably from about 11.5–12, i.e., metolazone-tris solutions.

The invention further provides solutions having extended stability that are suitable for parenteral administration comprising metolazone in a Bis-Tris or Tris buffer having a pH of from about 11.5 to 12.

Also included within the scope of the invention are methods for producing such solutions.

Still further, the invention provides solutions suitable for parenteral, e.g., intravenous, administration comprising an effective anti-hypertensive amount of metolazone in a Bis-Tris or Tris buffer having a pH of from about 11.5 to 12.

Yet further, the invention provides solutions suitable for parenteral administration comprising furosemide and metolazone in Bis-Tris or Tris buffer at a pH of from about 11.5 to about 12.

Further, the invention provides methods for treating an anti-hypertensive patient which comprises parenteral, e.g., intravenous, administration of an effective amount of a solution of metolazone in a Bis-Tris buffer.

The invention also encompasses methods for treating patients suffering from or affected by edema or edematious states comprising parenteral, e.g., intravenous, administration of an effective amount of a solution of metolazone in Tris buffer. Representative edematious states include, for example, congestive heart failure and hypertension.

Parenteral solutions comprising metolazone in Bis-Tris or Tris buffer according to the invention are typically prepared by mixing the required amount of metolazone, which may be purified prior to use, is mixed with the buffer and adding to the resulting solution sodium hydroxide or other suitable base until a pH of about 12 to 12.5 is reached. To this highly basic solution is then added a protic acid, such as, for example, acetic acid, preferably about 1 molar acetic acid, to adjust the pH of the solution to that at which metolazone is completely soluble. The process is preferably carried out at room temperature, although other temperatures are acceptable.

Most preferred solutions of metolazone and Bis-Tris or Tris buffer contain about 1 mg of metolazone per ml of solution. The concentration of Bis-Tris or Tris buffer in the solution is typically about 0.05M. The resulting solutions after cooling to room temperature may be sterilized by known means, e.g., ultra-filtration preferably a 13 mm, 0.45 micron filter, terminal autoclave heating, or ethylene oxide treatment and may be packaged into vials suitable for dispensing as parenteral products.

The preparation thus obtained at a pH of about 11.5 to 12 was found, quite unexpectedly, to remain in solution. The metolazone/Bis-Tris and metolazone/Tris aqueous formulations demonstrate remarkable stability when stored at room temperature over at least a three week period without the formation of turbidity or precipitate.

The solutions thus formulated are indicated for the treatment of hypertension, heart failure, or renal disease. Solutions may also be prepared in a similar manner to contain furosemide and metolazone. As with any potent drug, the dosage must be individualized by the treating clinician.

One skilled in the art will recognize that modifications may be made in the present invention without deviating from the spirit or scope of the invention. The invention is illustrated further by the following examples which are not to be construed as limiting the invention or scope of the specific procedures described herein.

EXAMPLE 1

To a mixture containing indicated quantities of metolazone (Research Biochemicals Inc., Lot #CC-1088E), cyclodextrin (American Maize Products Co.), and with or without polyvinyl pyrrolidones (Sigma Chemical Co.), in differing amounts, as well as a quantity (as indicated) of different buffers at different concentrations, were added. This mixture was stirred, and 5N NaOH solution was added dropwise until a clear solution resulted. The pH of this solution was generally between 12.0–12.5. (It was allowed to stand at room temperature for 30 minutes in cases where cyclodextrins were used). To this solution, 1M acetic acid was added in order to adjust to the desired pH at which the metolazone was completely soluble. The solution was filtered through 13 mm, 0.45 micron filter and stored in vials at room temperature and 40° C. for several days. The results of these experiments are reported below in Table 1.

TABLE 1

METOLAZONE SOLUBILITY

| Buffer Used (0.1M unless otherwise stated) | Final conc. Metolazone mg/ml | Final pH of Solution | Temp. for Storage | Observations on stability after standing for period of time | | | | | | |
|---|---|---|---|---|---|---|---|---|---|---|
| | | | | 24 hr | 48 hr | 72 hr | 96 hr | 1 Wk | 2 Wk | 3 Wk |
| 12 ml Na Acetate + 0.1 ml Tween 80 | 1 | 6.7 | RT | ppt | | | | | | |
| 12 ml Na Acetate + 0.1 ml Tween 80 | 1 | 9.0 | RT | ppt | | | | | | |
| 12 ml Na Acetate + 0.2 ml Tween 80 | 1 | 6 | RT | ppt | | | | | | |
| 12 ml Na Acetate + 0.5 ml Tween 80 | 1 | 6 | RT | ppt | | | | | | |
| 12 ml Na Acetate + 2 ml Tween 80 | 1 | 9.5 | RT | ppt | | | | | | |
| 12 ml Na Acetate + 3 ml Tween 80 | 1 | 10.0 | RT | ppt | | | | | | |
| 12 ml Na Acetate + 2 ml AMPSO[1] | 1.0 with 66 mg β CD | 10.0 | RT | Clear | Clear | ppt | | | | |
| 12 ml Na Acetate + 2 ml Bicine[2] | 1.0 with 66 mg β CD | 10.0 | RT | Clear | Clear | ppt | | | | |
| 12 ml Na Acetate + 2 ml Bis-Tris | 1.0 with 66 mg β CD | 10.0 | RT | Clear | Clear | ppt | | | | |
| 12 ml Na Acetate + 2 ml CAPS[3] | 1.0 with 66 mg β CD | 10.0 | RT | Clear | Clear | ppt | | | | |
| 12 ml Na Acetate + 2 ml CHES[4] | 1.0 with 66 mg β CD | 10.0 | RT | Clear | Clear | ppt | | | | |
| 12 ml Na Acetate + 2 ml Glycine | 1.0 with 66 mg β CD | 10.0 | RT | Clear | Clear | ppt | | | | |
| 12 ml Na Acetate + 2 ml TAPS[5] | 1.0 with 66 mg β CD | 10.0 | RT | Clear | Clear | ppt | | | | |
| 12 ml Na Acetate + 2 ml Tricine | 1.0 with 66 mg β CD | 10.0 | RT | Clear | Clear | ppt | | | | |
| 12 ml Na Acetate + 2 ml TEA | 1.0 with 66 mg β CD | 10.0 | RT | Clear | Clear | ppt | | | | |
| 12 ml Na Acetate + 2 ml Tris | 1.0 with 66 mg β CD | 10.0 | RT | Clear | Clear | ppt | | | | |
| 5% NaHCO$_3$ | 1.5 | 11 | RT | ppt | | | | | | |
| AMPSO | 2 | 9.5 | RT | ppt | | | | | | |
| AMPSO | 2 | 10.0 | RT | ppt | | | | | | |
| AMPSO | 2 | 10.5 | RT | ppt | | | | | | |
| AMPSO | 1 | 10.0 | RT | ppt | | | | | | |
| AMPSO | 1.0 with 66 mg β CD | 10.0 | RT | Clear | ppt | | | | | |
| AMPSO | 1.0 | 12.0 | RT | ppt | ppt | ppt | ppt | ppt | ppt | |
| AMPSO | 1.0 | 12.0 | 40° C. | ppt | ppt | ppt | ppt | ppt | ppt | |
| AMPSO | 2.0 | 11.5 | RT | ppt | ppt | ppt | ppt | ppt | ppt | |
| AMPSO | 2.0 | 11.5 | 40° C. | ppt | ppt | ppt | ppt | ppt | ppt | |
| AMPSO | 2.0 | 12.0 | RT | ppt | ppt | ppt | ppt | ppt | ppt | |
| AMPSO | 2.0 | 12.0 | 40° C. | ppt | ppt | ppt | ppt | ppt | ppt | |
| Bicine | 2 | 9.5 | RT | ppt | | | | | | |
| Bicine | 2 | 10.0 | RT | ppt | | | | | | |
| Bicine | 2 | 10.5 | RT | ppt | | | | | | |
| Bicine | 1 | 10.0 | RT | ppt | | | | | | |
| Bicine | 1.0 with 66 mg β CD | 10.0 | RT | Clear | Clear | ppt | | | | |
| Bicine 0.05 | 1 | 11.5 | RT | ppt | ppt | ppt | ppt | ppt | | |

TABLE 1-continued

METOLAZONE SOLUBILITY

| Buffer Used (0.1M unless otherwise stated) | Final conc. Metolazone mg/ml | Final pH of Solution | Temp. for Storage | Observations on stability after standing for period of time | | | | | | |
|---|---|---|---|---|---|---|---|---|---|---|
| | | | | 24 hr | 48 hr | 72 hr | 96 hr | 1 Wk | 2 Wk | 3 Wk |
| Bicine 0.05 | 1 | 11.5 | 40° C. | ppt | | | | | | |
| Bicine 0.05 | 1 | 12.0 | RT | ppt | ppt | ppt | ppt | ppt | | |
| Bicine 0.05 | 1 | 12.0 | 40° C. | ppt | | | | | | |
| Bicine 0.05 | 2 | 11.5 | RT | ppt | ppt | ppt | ppt | ppt | ppt | |
| Bicine 0.05 | 2 | 11.5 | 40° C. | ppt | ppt | ppt | ppt | ppt | ppt | |
| Bicine 0.05 | 2 | 12.0 | RT | ppt | ppt | ppt | ppt | ppt | ppt | |
| Bicine 0.05 | 2 | 12.0 | 40° C. | ppt | ppt | ppt | ppt | ppt | ppt | |
| Bis-Tris | 1.5 | 10.4 | RT | ppt | | | | | | |
| Bis-Tris | 2 | 9.5 | RT | ppt | | | | | | |
| Bis-Tris | 2 | 10.0 | RT | ppt | | | | | | |
| Bis-Tris | 2 | 10.5 | RT | ppt | | | | | | |
| Bis-Tris | 1 | 10.0 | RT | ppt | | | | | | |
| Bis-Tris | 1.0 with 66 mg β CD | 10.0 | RT | Clear | Clear | ppt | | | | |
| Bis-Tris 0.5M | 1.0 | 11.5 | RT | Clear | Clear | Clear | Clear | Clear | Clear | Clear |
| Bis-Tris 0.5M | 1.0 | 11.5 | 40° C. | Clear | Clear | Clear | Clear | Clear | Clear | Clear |
| Bis-Tris 0.5M | 1.0 | 12.0 | RT | Clear | Clear | Clear | Clear | Clear | Clear | Clear |
| Bis-Tris 0.5M | 1.0 | 12.0 | 40° C. | Clear | Clear | Clear | Clear | Clear | Clear | Clear |
| Bis-Tris 0.5M | 2.0 | 11.5 | RT | Clear | Clear | Clear | Clear | Clear | ppt | |
| Bis-Tris 0.5M | 2.0 | 11.5 | 40° C. | Clear | Clear | Clear | Clear | Clear | ppt | |
| Bis-Tris 0.5M | 2.0 | 12.0 | RT | Clear | Clear | Clear | Clear | Clear | ppt | |
| Bis-Tris 0.5M | 2.0 | 12.0 | 40° C. | Clear | Clear | Clear | Clear | Clear | ppt | |
| CAPS | 2 | 9.5 | RT | ppt | | | | | | |
| CAPS | 2 | 10.0 | RT | ppt | | | | | | |
| CAPS | 2 | 10.5 | RT | ppt | | | | | | |
| CAPS | 1 | 10.0 | RT | ppt | | | | | | |
| CAPS | 1.0 with 66 mg β CD | 10.0 | RT | Clear | Clear | ppt | | | | |
| CAPS | 1.5 | 11 | RT | ppt | | | | | | |
| CAPS | 1.5 | 10.4 | RT | ppt | | | | | | |
| CAPS 0.05 | 1.0 | 11.5 | RT | Clear | Clear | Clear | Clear | ppt | | |
| CAPS 0.05 | 1.0 | 11.5 | 40° C. | Clear | Clear | Clear | Clear | Clear | ppt | |
| CAPS 0.05 | 1.0 | 12.0 | RT | Clear | Clear | Clear | Clear | Clear | Clear | ppt |
| CAPS 0.05 | 1.0 | 12.0 | 40° C. | Clear | ppt | | | | | |
| CAPS 0.05 | 2.0 | 11.5 | RT | Clear | Clear | Clear | Clear | Clear | ppt | |
| CAPS 0.05 | 2.0 | 11.5 | 40° C. | Clear | Clear | Clear | Clear | Clear | ppt | |
| CAPS 0.05 | 2.0 | 12.0 | RT | Clear | Clear | Clear | Clear | Clear | ppt | |
| CAPS 0.05 | 2.0 | 12.0 | 40° C. | Clear | Clear | Clear | Clear | Clear | ppt | |
| CHES | 1 | 11.2 | RT | ppt | | | | | | |
| CHES | 1 | 10.8 | RT | ppt | | | | | | |
| CHES | 1 | 10.3 | RT | ppt | | | | | | |
| CHES | 1.5 | 10.4 | RT | ppt | | | | | | |
| CHES in D5W | 2 | 9.5 | RT | ppt | | | | | | |
| CHES in D5W | 2 | 10.0 | RT | ppt | | | | | | |
| CHES in D5W | 2 | 10.5 | RT | ppt | | | | | | |
| CHES in D5W | 1 | 10.0 | RT | ppt | | | | | | |
| CHES in D5W | 1.0 with 66 mg β CD | 10.0 | RT | Clear | Clear | ppt | | | | |
| CHES in D5W | 1 | 9.3 | RT | ppt | | | | | | |
| CHES in D5W 0.05 | 1 | 11.5 | RT | Clear | ppt | | | | | |
| CHES in D5W 0.05 | 1 | 11.5 | 40° C. | Clear | ppt | | | | | |
| CHES in D5W 0.05 | 1 | 12.0 | RT | Clear | ppt | | | | | |
| CHES in D5W 0.05 | 1 | 12.0 | 40° C. | Clear | ppt | | | | | |
| CHES in D5W 0.05 | 2 | 11.5 | RT | Clear | ppt | | | | | |
| CHES in D5W 0.05 | 2 | 11.5 | 40° C. | Clear | ppt | | | | | |
| CHES in D5W 0.05 | 2 | 12.0 | RT | Clear | ppt | | | | | |
| CHES in D5W 0.05 | 2 | 12.0 | 40° C. | Clear | ppt | | | | | |
| Glycine | 1 | 11.3 | RT | ppt | | | | | | |
| Glycine | 1 | 10.9 | RT | ppt | | | | | | |
| Glycine | 1 | 10.3 | RT | ppt | | | | | | |
| Glycine | 1.5 | 10.4 | RT | ppt | | | | | | |
| Glycine | 2 | 9.5 | RT | ppt | | | | | | |
| Glycine | 2 | 10.0 | RT | ppt | | | | | | |
| Glycine | 2 | 10.5 | RT | ppt | | | | | | |
| Glycine | 1 | 10.0 | RT | ppt | | | | | | |
| Glycine | 1.0 with 66 mg β CD | 10.0 | RT | Clear | Clear | ppt | | | | |
| $H_2O$ | 1 | 10.5 | RT | Clear | Clear | Color/ppt | | | | |
| $H_2O$ | 1 | 10.5 | 40° C. | Clear | Color/ppt | | | | | |
| $H_2O$ | 1 | 11.0 | RT | Clear | Clear | Color/ppt | | | | |
| $H_2O$ | 1 | 11.0 | 40° C. | Clear | ppt | | | | | |
| $H_2O$ | 2 | 10.5 | RT | Clear | Color | | | | | |
| $H_2O$ | 2 | 10.5 | 40° C. | Clear | ppt | | | | | |

TABLE 1-continued

METOLAZONE SOLUBILITY

| Buffer Used (0.1M unless otherwise stated) | Final conc. Metolazone mg/ml | Final pH of Solution | Temp. for Storage | Observations on stability after standing for period of time | | | | | | |
|---|---|---|---|---|---|---|---|---|---|---|
| | | | | 24 hr | 48 hr | 72 hr | 96 hr | 1 Wk | 2 Wk | 3 Wk |
| $H_2O$ | 2 | 11.0 | RT | Clear | Color/ppt | | | | | |
| $H_2O$ | 2 | 11.0 | 40° C. | Clear | ppt | | | | | |
| $H_2O$ | 1 | 11.0 | RT | Clear | Color/ppt | | | | | |
| $H_2O$ | 1 | 11.0 | 40° C. | Clear | Color/ppt | | | | | |
| $H_2O$ | 1 | 10.5 | RT | Clear | Color | | | | | |
| $H_2O$ | 1 | 10.5 | 40° C. | Clear | Color/ppt | | | | | |
| $H_2O$ | 2 | 10.5 | RT | Clear | Color/ppt | | | | | |
| $H_2O$ | 2 | 10.5 | 40° C. | Clear | Color | | | | | |
| $H_2O$ | 2 | 11.0 | RT | Clear | Color | | | | | |
| $H_2O$ | 2 | 11.0 | 40° C. | Clear | Color | | | | | |
| K-Phosphate 1.0M | 1.5 | 11 | RT | ppt | | | | | | |
| Na Acetate Buffer in D5W | 1 | 9.3 | RT | ppt | | | | | | |
| Na Acetate Buffer | 2 | 9.5 | RT | ppt | | | | | | |
| Na Acetate Buffer | 2 | 10.0 | RT | ppt | | | | | | |
| Na Acetate Buffer | 2 | 10.5 | RT | ppt | | | | | | |
| Na Acetate Buffer | 1 | 10.5 | RT | Clear | Clear | Clear | Clear | ppt | | |
| Na Acetate Buffer | 1 | 10.0 | RT | ppt | | | | | | |
| Na Acetate Buffer | 1 | 9.5 | RT | ppt | | | | | | |
| Na Acetate Buffer | 1 | 10.5 | RT | Clear | Clear | Clear | Clear | ppt | | |
| Na Acetate Buffer | 1 | 10.5 | 40° C. | Clear | Clear | Clear | Clear | ppt | | |
| Na Acetate Buffer | 1.0 with 88 mg βCD | 11 | RT | Clear | Clear | ppt | | | | |
| Na Acetate Buffer | 1.0 with 88 mg Encapcine | 11 | RT | Clear | ppt | ppt | | | | |
| Na Acetate Buffer | 1.0 with 88 mg β CD | 11 | RT | Clear | ppt | ppt | | | | |
| Na Acetate Buffer | 1.0 with 88 mg γ-CD | 11 | RT | Clear | ppt | | | | | |
| Na Acetate Buffer | 1.0 with 176 mg γ-CD | 9.8 | RT | Clear | Clear | ppt | | | | |
| Na Acetate Buffer | 1.0 with 440 mg γ-CD | 9.8 | RT | Clear | ppt | | | | | |
| Na Acetate Buffer | 1.0 with 44 mg β-CD | 10.5 | RT | Clear | Clear | Clear | Clear | ppt | | |
| Na Acetate Buffer | 1.0 with 44 mg βCD | 10.5 | 40° C. | Clear | Clear | Clear | Clear | ppt | | |
| Na Acetate Buffer | 1.0 with 66 mg β CD | 10.0 | RT | Clear | Clear | Clear | Clear | ppt | | |
| Na Acetate Buffer | 1.0 with 66 mg β CD | 10.0 | 40° C. | Clear | Clear | Clear | Clear | ppt | | |
| Na Acetate Buffer 95% ETOH(3:1) | 3 | 3.4 | RT | ppt | | | | | | |
| Na Acetate Buffer | 1.5 | 11 | RT | ppt | | | | | | |
| Na Acetate | 1.0 with 30 mg PVP (MW 40,000) Int Visc 26–35 | 9.5 | RT | ppt | | | | | | |
| Na Acetate | 1.0 with 30 mg PVP (MW 40,000) Int Visc 28–32 | 9.5 | RT | ppt | | | | | | |
| Na Acetate | 1.0 with 30 mg PVP (MW 10,000) Int Visc 12–18 | 9.5 | RT | ppt | | | | | | |
| Na Acetate | 1.0 with 5 mg PCP (MW 40,000) Int Visc 26–35 | 9.5 | RT | ppt | | | | | | |
| Na Acetate | 1.0 with 5 mg PVP (MW 40,000) Int Visc 28–32 | 9.5 | RT | ppt | | | | | | |
| Na Acetate | 1.0 with 5 mg PVP (MW 10,000) Int Visc 12–18 | 9.5 | RT | ppt | | | | | | |
| Saline | 1 | 10.5 | RT | Clear | Clear | Color | | | | |
| Saline | 1 | 10.5 | 40° C. | Clear | ppt | | | | | |
| Saline | 1 | 11.0 | RT | Clear | Color | | | | | |
| Saline | 1 | 11.0 | 40° C. | Clear | ppt | | | | | |
| Saline | 2 | 10.5 | RT | Clear | Color | | | | | |
| Saline | 2 | 10.5 | 40° C. | Clear | ppt | | | | | |
| Saline | 2 | 11.0 | RT | Clear | Clear | ppt | | | | |
| Saline | 2 | 11.0 | 40° C. | Clear | ppt | | | | | |
| Saline | 1 | 11.0 | RT | Clear | Color | | | | | |
| Saline | 1 | 11.0 | 40° C. | Clear | Color | | | | | |
| TAPS | 2 | 9.5 | RT | ppt | | | | | | |
| TAPS | 2 | 10.0 | RT | ppt | | | | | | |
| TAPS | 2 | 10.5 | RT | ppt | | | | | | |
| TAPS | 1.0 with 66 mg β CD | 10.0 | RT | Clear | Clear | ppt | | | | |
| TAPS 0.05 | 1 | 10.0 | RT | ppt | | | | | | |
| TAPS 0.05 | 1 | 11.5 | RT | Clear | Clear | Clear | Clear | Clear | ppt | |
| TAPS 0.05 | 1 | 11.5 | 40° C. | Clear | Clear | Clear | Clear | Clear | ppt | |
| TAPS 0.05 | 1 | 12.0 | RT | Clear | Clear | Clear | Clear | Clear | ppt | |
| TAPS 0.05 | 1 | 12.0 | 40° C. | Clear | Clear | Clear | Clear | Clear | ppt | |
| TAPS 0.05 | 2 | 11.5 | RT | Clear | ppt | | | | | |
| TAPS 0.05 | 2 | 11.5 | 40° C. | Clear | ppt | | | | | |

TABLE 1-continued

METOLAZONE SOLUBILITY

| Buffer Used (0.1M unless otherwise stated) | Final conc. Metolazone mg/ml | Final pH of Solution | Temp. for Storage | Observations on stability after standing for period of time | | | | | | |
|---|---|---|---|---|---|---|---|---|---|---|
| | | | | 24 hr | 48 hr | 72 hr | 96 hr | 1 Wk | 2 Wk | 3 Wk |
| TAPS 0.05 | 2 | 12.0 | RT | Clear | ppt | | | | | |
| TAPS 0.05 | 2 | 12.0 | 40° C. | Clear | ppt | | | | | |
| TEA | >1 | 10.5 | RT | ppt | | | | | | |
| TEA | >1 | 10.5 | 40° C. | ppt | | | | | | |
| TEA | >1 | 11.0 | RT | ppt | | | | | | |
| TEA | >1 | 11.0 | 40° C. | ppt | | | | | | |
| TEA | >1 | 11.5 | RT | ppt | | | | | | |
| TEA | >1 | 11.5 | 40° C. | ppt | | | | | | |
| TEA | 1.0 with 66 mg β CD | 10.0 | RT | Clear | Clear | ppt | | | | |
| TEA + 1.8% NaCl (1:1) | >1 | 10.5 | RT | ppt | | | | | | |
| TEA + 1.8% NaCl (1;1) | >1 | 11.0 | RT | ppt | | | | | | |
| TEA + 1.8% NaCl (1:1) | >1 | 11.5 | RT | ppt | | | | | | |
| TEA + 1.8% NaCl (1:1) | 2 | 9.5 | RT | ppt | | | | | | |
| TEA + 1.8% NaCl (1:1) | 2 | 10.0 | RT | ppt | | | | | | |
| TEA + 1.8% NaCl (1:1) | 2 | 10.5 | RT | ppt | | | | | | |
| TEA + 1.8% NaCl (1:1) | 1 | 10.0 | RT | ppt | | | | | | |
| TEA + 1.8% NaCl (1:1) | 1 | 11.5 | RT | Clear | Clear | ppt | | | | |
| TEA + 1.8% NaCl (1:1) | 1 | 11.5 | 40° C. | Clear | ppt | | | | | |
| TEA + 1.8% NaCl (1:1) | 1 | 12.0 | RT | Clear | ppt | | | | | |
| TEA + 1.8% NaCl (1:1) | 1 | 12.0 | 40° C. | Clear | ppt | | | | | |
| TEA + 1.8% NaCl (1:1) | 2 | 11.5 | RT | Clear | ppt | | | | | |
| TEA + 1.8% NaCl (1:1) | 2 | 11.5 | 40° C. | Clear | ppt | | | | | |
| TEA + 1.8% NaCl (1:1) | 2 | 12.0 | RT | Clear | ppt | | | | | |
| TEA + 1.8% NaCl (1:1) | 2 | 12.0 | 40° C. | Clear | ppt | | | | | |
| Tricine[6] | 1 | 11.3 | RT | ppt | | | | | | |
| Tricine | 1 | 11.0 | RT | ppt | | | | | | |
| Tricine | 1 | 10.4 | RT | ppt | | | | | | |
| Tricine | 1.5 | 10.4 | RT | ppt | | | | | | |
| Tricine | 2 | 9.5 | RT | ppt | | | | | | |
| Tricine | 2 | 10.0 | RT | ppt | | | | | | |
| Tricine | 2 | 10.5 | RT | ppt | | | | | | |
| Tricine | 1 | 10.0 | RT | ppt | | | | | | |
| Tricine | 1.0 with 66 mg β CD | 10.0 | RT | Clear | Clear | ppt | | | | |
| Tricine 0.05 | 1 | 11.5 | RT | Clear | Clear | Clear | Clear | Clear | Clear | ppt |
| Tricine 0.05 | 1 | 11.5 | 40° C. | Clear | ppt | | | | | |
| Tricine 0.05 | 1 | 12.0 | RT | Clear | Clear | Clear | Clear | Clear | Clear | ppt |
| Tricine 0.05 | 1 | 12.0 | 40° C. | Clear | ppt | | | | | |
| Tricine 0.05 | 2.0 | 11.5 | RT | Clear | Clear | Clear | Clear | Clear | ppt | |
| Tricine 0.05 | 2.0 | 11.5 | 40° C. | Clear | Clear | Clear | Clear | Clear | ppt | |
| Tricine 0.05 | 2.0 | 12.0 | RT | Clear | Clear | Clear | Clear | Clear | ppt | |
| Tricine 0.05 | 2.0 | 12.0 | 40° C. | Clear | Clear | Clear | Clear | Clear | ppt | |
| TEA | 1 | 11.3 | RT | ppt | | | | | | |
| TEA | 1 | 10.9 | RT | ppt | | | | | | |
| TEA | 1 | 10.6 | RT | ppt | | | | | | |
| TEA | 2 | 9.5 | RT | ppt | | | | | | |
| TEA | 2 | 10.0 | RT | ppt | | | | | | |
| TEA | 2 | 10.5 | RT | ppt | | | | | | |
| TEA | 1 | 10.0 | RT | ppt | | | | | | |
| TEA | 1.5 | 10.4 | RT | ppt | | | | | | |
| Tris | 1.5 | 10.4 | RT | ppt | | | | | | |
| Tris | 1.5 | 7.5 | RT | ppt | | | | | | |
| Tris | 1.5 | 10.4 | RT | ppt | | | | | | |
| Tris | 1.5 | 10.1 | RT | ppt | | | | | | |
| Tris | 2 | 10.8 | RT | ppt | | | | | | |
| Tris | 5 | 11.2 | RT | ppt | | | | | | |
| Tris | 10 | 12 | RT | ppt | | | | | | |
| Tris | 2 | 9.5 | RT | ppt | | | | | | |

TABLE 1-continued

METOLAZONE SOLUBILITY

| Buffer Used (0.1M unless otherwise stated) | Final conc. Metolazone mg/ml | Final pH of Solution | Temp. for Storage | Observations on stability after standing for period of time | | | | | | |
|---|---|---|---|---|---|---|---|---|---|---|
| | | | | 24 hr | 48 hr | 72 hr | 96 hr | 1 Wk | 2 Wk | 3 Wk |
| Tris | 2 | 10.0 | RT | ppt | | | | | | |
| Tris | 2 | 10.5 | RT | ppt | | | | | | |
| Tris | 1 | 10.0 | RT | ppt | | | | | | |
| Tris | 1.0 with 66 mg β CD | 10.0 | RT | Clear | Clear | ppt | | | | |

[1]3-[(1,1-dimethyl-2-hydroxyethyl)amino]-2-hydroxypropanesulfonic acid.
[2]N,N-bis-(2-hydroxyethyl)glycine
[3]3-(cyclohexylamino)propanesulfonic acid
[4]2-(cyclohexylamino)ethanesulfonic acid
[5]3-([tris-hydroxymethyl)methyl]amino)propanesulfonic acid
[6]N-[tris-hydroxymethyl)methyl]glycine

TABLE 2

METOLAZONE SOLUBILITY

| Buffer Used (0.1M unless otherwise stated) | Final conc. Metolazone mg/ml | Final pH of Solution | Temp. for Storage | 24 hr | 48 hr | 72 hr | 96 hr | 1 Wk | 3 Wk | 10 Wks | On-going |
|---|---|---|---|---|---|---|---|---|---|---|---|
| *Tris 0.05 | 1 | 11.5 | RT | Clear | Clear | Clear | Clear | Clear | Clear | Clear | Clear |
| *Tris 0.05 | 1 | 11.5 | 40° C. | Clear | Clear | Clear | Clear | Clear | Clear | Clear | Clear |
| *Tris 0.05 | 1 | 12.0 | RT | Clear | Clear | Clear | Clear | Clear | Clear | Clear | Clear |
| *Tris 0.05 | 1 | 12.0 | 40° C. | Clear | Clear | Clear | Clear | Clear | Clear | Clear | Clear |
| *Tris 0.05 | 1 | 11.5 | RT | Clear | Clear | Clear | Clear | Clear | Clear | Clear | Clear |
| *Tris 0.05 | 1 | 11.5 | 40° C. | Clear | Clear | Clear | Clear | Clear | Clear | Clear | Clear |
| *Tris 0.05 | 1 | 12.0 | RT | Clear | Clear | Clear | Clear | Clear | Clear | Clear | Clear |
| *Tris 0.05 | 1 | 12.0 | 40° C. | Clear | Clear | Clear | Clear | Clear | Clear | Clear | Clear |

GRAPH CODES
RT = Room Temperature
CD = Cyclodextrin
PVP = Polyvinylpyrrolidone
TEA = Triethanolamine
*Solutions remained colorless unless indicated otherwise As the above data demonstrates, Metolazone is unexpectedly stable as a formulation in 0.05M Bis-Tris at pHs from about 11.5 to 12.0 and as a formulation in 0.05M Tris at pHs from about 11.5 to 12.0.

The activity of metolazone dissolved in the buffer systems of the invention is demonstrated by the following examples. In examples 2–4 below rats are deprived of food and water. After 24 hours, water only (25 ml/kg) is given orally and a solution of the drug, i.e., lasix or metolazone, is given intraperitoneally. Urine is collected during the following 24 hours. The results of each example are shown in the accompanying table.

EXAMPLE 2

Metolazone Rat Experiment

Rats 450 gms received 2 mg/kg Metolazone intraperitoneally in tris buffer. Group I Control received Tris containing no metolazone, Group II (rats originally used in saline control experiments) received 1 ml of a solution containing 1 mg/ml (2 mg/kg dose) metolazone in 0.05M Tris at pH 11.5 to 12. Group III were animals (not previously treated) receiving 1 ml of a solution of 1 mg/ml (2 mg/kg dose) in Tris buffer metolazone. The volume of urine produced by the rats is shown below in Table III.

TABLE III

Diuretic Effect of Metolazone (IP route in Rats (Values indicate amount (ml) of urine collected)

| Rat No. | Group I IP Tris buffer (1 ml) (Control Group) | Group II IP Metolazone 2 mg/kg 1 ml (1 mg/ml) in Tris buffer (Rats from control group used) | Group III IP Metolazone 2 mg/kg 1 ml (1 mg/ml) in Tris buffer (different rats used) |
|---|---|---|---|
| 1 | 8 | 16 | 22 |
| 2 | 7 | 15 | 15 |
| 3 | 9 | 17 | 15 |
| 4 | 10 | 18 | 12 |
| 5 | 10 | 17 | 13 |
| Mean ± SD | 9 ± 1 | 17 ± 1** | 16 ± 3** |

**Results from Goups II and III when compared to control Group I, were significantly different ($p < 0.01$)

EXAMPLE 3

Lasox Rat Experiment

Sprague-Dawley rats, 450–500 g, received saline or furosemide (Lasix) in normal saline intraperitoneally at the concentrations listed below in a 1 ml volume. The volume of urine produced by the animals is shown in Table 2.

Group I (5 rats) was administered 1 ml of normal saline intraperitoneally. Group II (5 rats) was originally used in saline controls) administered 1 ml of a 2 mg/ml Lasix/saline solution intraperitoneally (4 mg/kg dose).

Group III (5 previously untreated rats) was administered 1 ml of a 2 mg/ml Lasix/saline solution intraperitoneally (4 mg/kg dose). Group IV (5 previously untreated rats) was administered 1 ml of a 1 mg/ml Lasix/saline solution intraperitoneally (2 mg/kg dose). This diuretic effect of these formulations is shown below in Table IV.

TABLE V

Diuretic effect of Furosemide (Lasix) and Metolazone (IV route) combination therapy.

| Rat No. | Group (n = 5) IP lasix 4 mg/kg, 0.5 ml (4 mg/ml) in normal saline and IP metolazone 2 mg/kg, 0.5 mg (2 mg/ml) in Tris Buffer. (Rats employed that did not previously receive therapy) Volume of Urine Collected (ml) |
|---|---|
| 1 | 22 |
| 2 | 22 |
| 3 | 20 |
| 4 | 20 |
| 5 | 22 |
| mean ± SD | 21 ± 1 |

TABLE IV

Diuretic Effect of Furosemide (Lasix) in Rats (IP route) (Values indicate amount (ml) of urine collected)

| Rat No. | Group I IP Normal saline (1 ml) (Control group) | Group II IP Lasix 4 mg/kg 1 ml (2 mg/ml) in normal saline (Rats from control group used) | Group III IP Lasix 4 mg/kg 1 ml (2 mg/ml) in normal saline (previously untreated rats) | Group IV IP Lasix 2 mg/kg 1 ml (1 mg/ml) in normal saline (previously untreated rats) |
|---|---|---|---|---|
| 1 | 3 | 17 | 16 | 10 |
| 2 | 2 | 15 | 17 | 10 |
| 3 | 3 | 17 | 13 | 7 |
| 4 | 2 | 19 | 12 | 8 |
| 5 | 3 | 19 | 13 | 9 |
| Avg. ± SD | 3 ± 0.5 | 17 ± 2** | 14 ± 2** | 9 ± 1** |

**P results from Groups II, III, and IV when compared to control Group I, were significantly different ($p < 0.01$).

EXAMPLE 4

Diuretic Effects of Metolazone/Lasix Combination Therapy

Rats (450 g previously untreated) were intraperitoneally administered 0.5 ml of 4 mg/ml lasix solution (4 mg/kg dose) and 0.5 ml of 2 mg/ml metolazone/tris buffer solution, pH 11.5, (2 mg/kg dose). The results are shown in Table V below.

The results of these examples demonstrate that metalozone and lasix have distinctive action, increasing urine output. When lasix and metalozone are used in combination therapy the action is synergistic with more diuretic effect than with either drug alone.

From the foregoing it will be appreciated that, although specific embodiments of the invention have been described herein for purposes of illustration, various modifications may be made without deviating from the spirit and scope of the invention.

What is claimed:

1. A solution suitable for parenteral administration comprising a compound of the formula

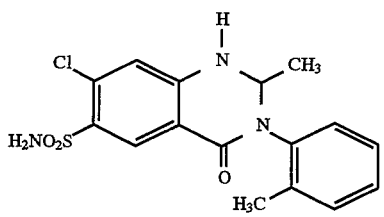

dissolved in an aqueous Tris buffer system having a pH of from about 10.5 to 12.5.

2. A solution suitable for parenteral administration comprising metolazone dissolved in an aqueous Tris buffer system having a pH of from about 10.5 to 12.5.

3. A solution according to claim 1 which comprises from about 0.01 to 1 mg per ml of metolazone in about 0.5M Tris buffer solution having a pH of about 11.5 to 12.

4. A method for the treatment of a patient suffering from hypertension, congestive heart failure or edema which comprises the intravenous administration of an effective amount of a solution according to claim 1.

5. A method for the preparation of a solution according to claim 1 which comprises forming a mixture of metolazone and Tris buffer at a pH of about 10.5 to 12.5.

6. A method for the treatment of a patient suffering from edema which comprises the intravenous administration of a solution according to claim 3.

7. A solution comprising an effective diuretic amount of a mixture of furosemide and metolazone in Tris buffer at a pH of from about 11.5 to 12.

* * * * *